US00PP23287P2

(12) United States Plant Patent
MacKenzie

(10) Patent No.: US PP23,287 P2
(45) Date of Patent: Dec. 25, 2012

(54) ***SEDUM* PLANT NAMED 'NONOGO'**

(50) Latin Name: *Sedum spurium*
Varietal Denomination: Nonogo

(75) Inventor: David MacKenzie, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 0 days.

(21) Appl. No.: 13/200,657

(22) Filed: Sep. 28, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Kent L Bell
(74) *Attorney, Agent, or Firm* — Penny J. Aguirre

(57) ABSTRACT

A new cultivar of *Sedum* plant, 'Nonogo', characterized by its deciduous foliage that emerges red-purple and maintains this color until fall leaf drop, its pink flowers in mid summer that emerge from pink flower buds and are arranged in flat-topped inflorescences carried a couple of inches above the foliage, and its low growing and procumbent growth habit.

1 Drawing Sheet

Botanical classification: *Sedum spurium.*
Variety denomination: 'Nonogo'.

CROSS REFERENCE TO A RELATED APPLICATION

This application is co-pending with a U.S. Plant Patent Application filed by the same Inventor that pertain to a plant derived from the same species, but not the same parentage, the Application is entitled *Sedum* Plant Named 'Nonom' (U.S. Plant patent application Ser. No. 13/200,670).

BACKGROUND OF THE INVENTION

The present invention relates to a new and distinct cultivar of *Sedum* plant, botanically known as *Sedum spurium* 'Nonogo' and will be referred to hereinafter by its cultivar name, 'Nonogo'. The new cultivar of *Sedum* is a hardy herbaceous perennial grown for use as a landscape and container plant and is particularly suitable as a groundcover.

'Nonogo' was discovered in March of 2008 as a naturally occurring bud mutation of *Sedum spurium* 'Schorbusser Blut' (not patented, syn. 'Dragon's Blood') that was growing in a field amongst 5,000 mature plants of 'Schorbusser Blut'.

Asexual reproduction of the new cultivar was first accomplished by stem cuttings in June of 2008 in Nunica, Mich. Propagation by cuttings and crown division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Nonogo' as a unique cultivar of *Sedum.*

1. 'Nonogo' exhibits foliage that emerges red-purple in color and holds this color until fall leaf drop.
2. 'Nonogo' exhibits flower buds that are pink in color.
3. 'Nonogo' exhibits flat-topped inflorescences with flowers that are pink in color and present in early summer.

4. 'Nonogo' exhibits a dense, low growing habit with foliage that reaches about 5 inches in height.

The parent plant, 'Schorbusser Blut', differs in having medium green to green with red margins and in having red flowers. 'Nonogo' can be compared to cultivars from the same Inventor; 'Nonov' (U.S. Plant Pat. No. 22,154) and 'Nonom'. 'Nonom' differs in having leaves that emerge glossy yellow-green and stay this color until fall leaf drop and in having red-purple flower buds, and 'Nonov' differs in having foliage that is darker reddish purple in color and in having pinkish purple flowers. 'Nonogo' can be compared to the following cultivars of *Sedum spurium* (all unpatented); 'Bronze Carpet' differs in having variable green/maroon leaves and deep pink flowers, 'Coccineum' differs in having green leaves and red flowers, 'Elizabeth' differs in having variable green or maroon leaves and pink flowers, 'Fuldaglut' differs in having maroon leaves and pink flowers, 'Red Carpet' differs in having red leaves and pink flowers, 'Royal Pink' and 'Summer Glory' differ in having green leaves and pink flowers, and 'Tricolor' differs in having leaves that are green with white edges and pink flowers.

BRIEF DESCRIPTION OF THE DRAWINGS

The accompanying colored photograph illustrates the overall appearance and distinct characteristics of the new *Sedum*. The photograph was taken of a 2 year-old plants of 'Nonogo' as grown in the ground in full sun in Nunica, Mich. The photograph in FIG. 1 illustrates the unique foliage coloration of 'Nonogo'. The colors in the photographs may differ slightly from the color values cited in the detailed botanical description, which accurately describe the colors of the new *Sedum.*

DETAILED BOTANICAL DESCRIPTION

The following is a detailed description of the new cultivar as observed on 2 year-old plants of 'Nonogo' as grown in the ground in full sun in Nunica, Mich. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period*.—The last two to three weeks of June to the first or second week of July in Michigan.

*Plant habit*.—Herbaceous perennial, dense, low growing habit, mature plant sprawl from central crown with procumbent stems rooting as they contact the ground.

*Height and spread*.—Reaches about 5 inches in height (foliage) and 11 inches in bloom, maximum spread is about 2 feet.

*Hardiness*.—Reliably in U.S.D.A. Zones 4B to 7B.

*Disease and pests*.—No susceptibility or resistance to diseases or pests has been observed.

*Propagation*.—Stem cuttings spring through summer and crown division throughout the year.

*Roots*.—Fibrous.

*Growth rate*.—Moderate.

Stem description:

*Stem shape*.—Round.

*Stem size*.—8 to 10 inches in length and about ⅛ inch in width.

*Internode length*.—Ranges from ⅛ to ¼ inch.

*Stem color*.—59B.

*Stem surface*.—Glabrous.

*Branching habit*.—Sparsely branched.

Foliage description:

*Leaf shape*.—Acicular.

*Leaf division*.—Simple.

*Leaf arrangement*.—Alternate.

*Leaf base*.—Truncate.

*Leaf apex*.—Broadly acute-rounded.

*Leaf venation*.—Not conspicuous, color matched leaf color.

*Leaf margins*.—Smooth, young leaves papilose-ciliate.

*Leaf attachment*.—Sessile.

*Leaf presence and orientation*.—Ascending.

*Leaf surface*.—Glabrous and waxy on upper and lower surface.

*Leaf color*.—Young and maturity leaves are colored 59A with the base of the leaves 144A on both surfaces.

*Leaf size*.—Young leaves; an average of ¼ inch length and 1/16 inch in width, mature leaves; an average of ¾ inches in length and ⅛ inch width.

Flower description:

*Inflorescence type*.—Terminal, cymose, drooping and sub-globose in bud, erect and flat in flower, concave in fruit, branches short and forked, dense, many flowered, sparingly leafy.

*Inflorescence size*.—An average of 2 inches in width and 1 inch in depth.

*Lastingness of inflorescence*.—About one month.

*Flower type*.—Perfect, spreading, 5-starred.

*Flower number*.—30 to 40 flowers per cyme.

*Flower fragrance*.—None.

*Flower buds*.—Conical in shape, about ⅜ inch in length and 3/16 inch in diameter, ribbed surface, 7A in color.

*Flower size*.—About ½ inch in length and ¾ inch in diameter.

*Peduncles*.—Round, range from ½ to ¾ inch in length, ⅛ inch in width, 59C in color, glabrous surface.

*Pedicels*.—Round, ¼ inch in length, ⅛ inch in width, 59C in color, glabrous surface.

*Sepals*.—5, spreading, ovate to lanceolate in shape, about ⅜ inch in length and ⅛ inch in width, 59D in color on both surfaces, entire margin, acute apex, truncate base, glabrous on both surfaces.

*Petals*.—5, spreading, lanceolate in shape, truncate base, acute apex, entire margin, color of inner and outer surfaces is 63B, glabrous on both surfaces.

Reproductive organs:

*Pistils*.—5, held erect, about ⅜ inch in length, stigma 1/32 inch in width and 151D in color, styles ¼ inch in length and 151D in color, ovary 1/10 inch in diameter and 151D in color.

*Stamens*.—10, about ⅜ inch in length, filament 151B in color, anther 151C in color, pollen is sparse in quantity and 151D in color.

*Fruit*.—Rounded with pointed tip, aggregate, range from 1/16 to ⅛ inch in length and ¼ inch in width, 151D in color, seed production was not observed.

It is claimed:

1. A new and distinct variety of *Sedum* plant named 'Nonogo' as described and illustrated herein.

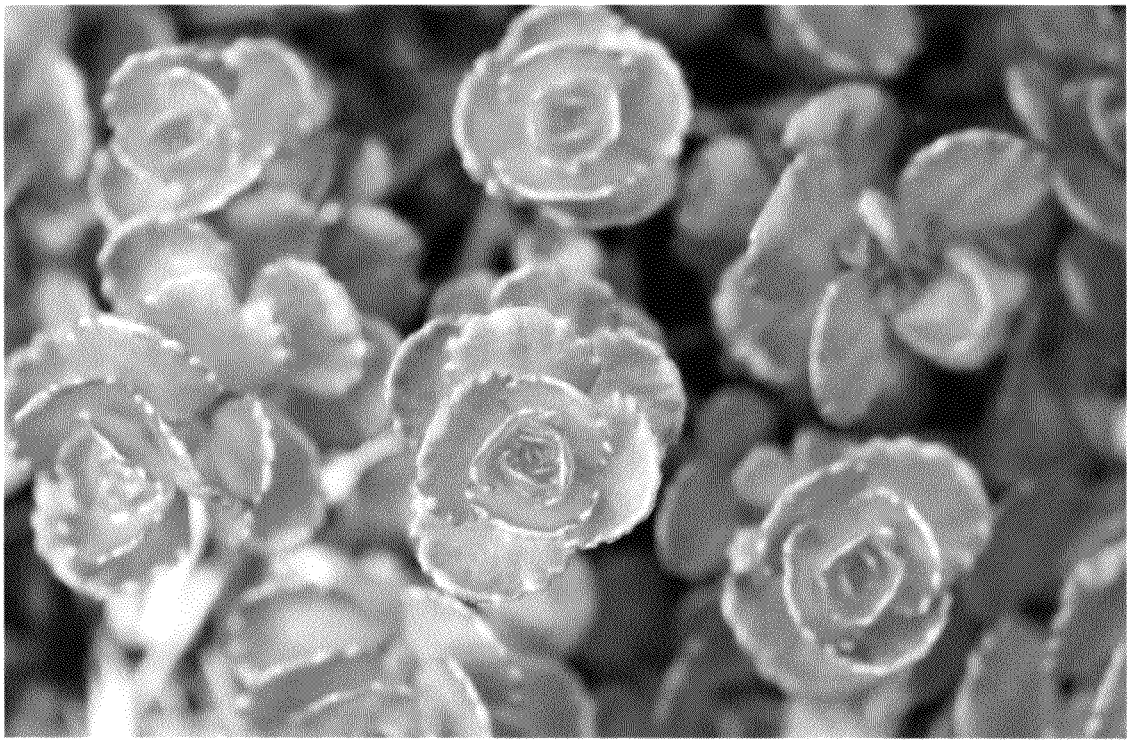

* * * * *